(12) United States Patent
Daniels et al.

(10) Patent No.: US 6,960,337 B2
(45) Date of Patent: Nov. 1, 2005

(54) METHODS AND COMPOSITIONS FOR TREATING BENIGN GYNECOLOGICAL DISORDERS

(75) Inventors: Anne-Marie Daniels, Pacific Palisades, CA (US); John R. Daniels, Pacific Palisades, CA (US); Malcolm C. Pike, Marina Del Rey, CA (US); Darcy V. Spicer, La Canada, CA (US)

(73) Assignee: Balance Pharmaceuticals, Inc., Santa Monica, CA (US)

(*) Notice: Subject to any disclaimer, the term of this patent is extended or adjusted under 35 U.S.C. 154(b) by 168 days.

(21) Appl. No.: 10/298,851

(22) Filed: Nov. 15, 2002

(65) Prior Publication Data

US 2004/0023867 A1 Feb. 5, 2004

Related U.S. Application Data

(60) Provisional application No. 60/400,626, filed on Aug. 2, 2002.

(51) Int. Cl.[7] .......................... A61K 9/12; A61K 31/56; A61F 2/02
(52) U.S. Cl. .......................... 424/45; 424/434; 424/426; 424/239; 514/2; 514/841; 514/843; 514/874; 514/58
(58) Field of Search .......................... 424/45, 434, 426, 424/239; 514/2, 841, 843, 874, 58

(56) References Cited

U.S. PATENT DOCUMENTS

| | | | |
|---|---|---|---|
| 4,315,925 A | 2/1982 | Hussain et al. |
| 4,383,993 A | 5/1983 | Hussain et al. |
| 4,476,116 A | 10/1984 | Anik |
| 4,596,795 A | 6/1986 | Pitha |
| 4,659,696 A | 4/1987 | Hirai et al. |
| 4,724,064 A | 2/1988 | Reid |
| 5,089,482 A | 2/1992 | Hermens et al. |
| 5,116,817 A | 5/1992 | Anik |
| 5,130,137 A | 7/1992 | Crowley, Jr. |
| 5,211,952 A | 5/1993 | Spicer et al. |
| 5,296,468 A | 3/1994 | Hoeger et al. |
| 5,340,584 A | 8/1994 | Spicer et al. |
| 5,340,585 A | 8/1994 | Pike et al. |
| 5,340,586 A | 8/1994 | Pike et al. |
| 5,681,817 A | 10/1997 | Hodgen et al. |
| 5,955,454 A | 9/1999 | Merkus |
| 5,977,070 A | 11/1999 | Piazza et al. |
| 6,225,298 B1 | 5/2001 | Spicer et al. |
| 2001/0016578 A1 | 8/2001 | Spicer et al. |

FOREIGN PATENT DOCUMENTS

| | | |
|---|---|---|
| EP | 0 709 099 A2 | 5/1996 |
| EP | 0 538 443 B1 | 10/1997 |
| WO | WO 92/01440 | 2/1992 |
| WO | WO 92/18107 | 10/1992 |
| WO | WO 94/26207 | 11/1994 |
| WO | WO 94/26208 | 11/1994 |
| WO | WO 96/15794 | 5/1996 |

OTHER PUBLICATIONS

Hermens, W., et al., *Pharmaceutical Research* 7(5):500–503, (1990).
Hermens, W., *Pharmaceutisch Weekblad Scientific Edition* 14(4A): 253–257, (1992).
Sugimoto, A.K., et al., *Fetrility and Sterility* 60(4):672–674, (1993).

*Primary Examiner*—Gary Kunz
*Assistant Examiner*—Mina Haghighatian
(74) *Attorney, Agent, or Firm*—Judy M. Mohr; Perkins Coie LLP

(57) ABSTRACT

An improvement in a method of treating benign gynecological disorders is described. In the method, treatment of a benign gynecological disorder with a composition comprised of a gonadotropin releasing hormone (GnRH) compound and an estrogenic compound, and optionally, an androgenic compound, is extended to premenopausal women who are not receiving an exogenously supplied progestin on a regular or periodic basis. Treatment in accord with the invention does not increase significantly the risk of endometrial hyperplasia. The method is also suitable for contraception.

7 Claims, 2 Drawing Sheets

```
                          SEQUENCE LISTING

<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 10
<223> OTHER INFORMATION: amino acid linked to NH2

<400> SEQUENCE: 1

Glu His Trp Ser Tyr Gly Leu Arg Pro Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 6
<223> OTHER INFORMATION: Xaa = Any Amino Acid in D configuration
<220> FEATURE:
<221> NAME/KEY: VARIANT
<222> LOCATION: 10
<223> OTHER INFORMATION: Amino Acid linked to NH2

<400> SEQUENCE: 2

Glu His Trp Ser Tyr Xaa Leu Arg Pro Gly
1               5                   10

<210> SEQ ID NO 3
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 6
<223> OTHER INFORMATION: Amino Acid in D configuration
<220> FEATURE:
<221> NAME/KEY: VARIANT
<222> LOCATION: 9
<223> OTHER INFORMATION: Amino Acid linked to ethylamide

<400> SEQUENCE: 3

Pro His Trp Ser Tyr Trp Leu Arg Pro
1               5

<210> SEQ ID NO 4
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 6
<223> OTHER INFORMATION: Amino Acid in D configuration
<220> FEATURE:
```

```
-continued
<221> NAME/KEY: VARIANT
<222> LOCATION: 10
<223> OTHER INFORMATION: Amino Acid linked to NH2

<400> SEQUENCE: 4

Glu His Trp Ser Tyr Ala Leu Arg Pro Gly
1               5                   10
```

METHODS AND COMPOSITIONS FOR TREATING BENIGN GYNECOLOGICAL DISORDERS

This application claims the benefit of U.S. Provisional Application No. 60/400,626, filed Aug. 2, 2002, incorporated herein by reference in its entirety.

FIELD OF THE INVENTION

The present invention relates to a method for treating benign gynecological disorders and to a method of contraception by administration of a composition comprised of a gonadotropin releasing hormone (GnRH) compound and an estrogenic compound, and optionally, an androgenic compound.

BACKGROUND OF THE INVENTION

During a woman's reproductive life, a delicate and complex interplay of hormones are timed and controlled by the hypothalamus. The hormones that participate in the feedback system regulating the menstrual cycle include estrogens and progesterone, the pituitary gonadotropins FSH (follicle stimulating hormone) and LH (luteinizing hormone), and gonadotropin-releasing hormone (GnRH) from the hypothalamus.

The menstrual cycle is usually divided into a follicular or proliferative phase and a luteal or secretory phase. The length of a normal menstrual cycle is defined as the time from the onset of one menstrual bleeding episode to the onset of the next. Towards the end of one menstrual cycle, plasma levels of estrogen and progesterone fall. Approximately a week prior to ovulation, estradiol levels begin to rise. Just prior to ovulation, estradiol secretion reaches a peak and then falls before rising again after ovulation. Plasma progesterone begins to rise just prior to midcycle and reaches its peak during the luteal phase.

During a women's reproductive years, defined as the time between onset of menses (menarche) and the final episode of menstrual bleeding (menopause), that is a premenopausal woman, a variety of benign gynecological disorders can occur. Common benign gynecological disorders include, but are not limited to, premenstrual syndrome, endometriosis, uterine leiomyomata (uterine fibroids), and polycystic ovarian syndrome. Administration of one or more of the hormones involved in regulation of the menstrual cycle has been proposed for relief of the symptoms associated with the disorder or for treatment of the symptoms related to the disorder.

For example, hormonal therapy has been contemplated for management of premenstrual syndrome, including its most severe form, namely late luteal phase dysphoric disorder. The essential feature of premenstrual syndrome is a pattern of clinically significant emotional and behavioral symptoms that occur during the last week of the luteal phase and remit within a few days after the onset of menstruation. In most females, these symptoms occur in the week before and remit within a few days after the onset of menses. Non-menstruating females who have had a hysterectomy but retain ovarian function may also report similar symptoms. Commonly experienced symptoms of premenstrual syndrome include marked affective lability (e.g., sudden episodes of sadness or irritability), persistent feelings of irritability, anger or tension, feelings of depression and self-deprecating thoughts, decreased interest in usual activities, fatigue and loss of energy, a subjective sense of difficulty in concentrating, changes in appetite, cravings for specific foods, sleep disturbance, breast tenderness or swelling, headaches, joint or muscle pain, a sensation of bloating, and weight gain. The symptoms are often so severe as to seriously interfere with work or with usual social activities or relationships with others.

Uterine leiomyomata (uterine fibroids) is another common disorder, with one in four women affected at some point in her reproductive life HARRISON'SPRINCIPLES OFINTERNALMEDICINE, 12$^{th}$ Ed. Wilson, J. et al. Eds., McGraw-Hill, New York, 1991). Many of the women with leiomyoma are asymptomatic and the diagnosis is made during a routine pelvic examination. The condition, however, can be associated with excessive menstrual bleeding or significant pelvic pain.

Endometriosis is another benign disorder characterized by the presence and proliferation of tissue resembling endometrium outside the endometrial cavity. The disorder is frequently associated with pelvic pain.

Polycystic ovarian disease is another benign disorder that is characterized by chronic anovulation, infertility, hirsutism, obesity, and amenorrhea or oligomenorrhea.

Hormonal therapy is one approach to treating such benign gynecological disorders. In particular, therapy with a compound that inhibits or suppressesgonadotropin releasing hormone (GnRH) has been proposed. GnRH, also known as luteinizing hormone releasing hormone (LHRH), is produced by the hypothalamus, as noted above. Synthetic agonists and antagonists of GnRH administered to premenopausal women have been shown to produce a sustained suppression of FSH/LH release after, in the case of agonists, a transient rise in FHS/LH. Thus, both GnRH agonists and GnRH antagonists are able to reduce serum estradiol and serum progesterone levels. However, a reduced level of the sex hormones is often accompanied by side effects including hot flashes, fatigue, headache, depression, decreased libido, and most significantly, loss of bone mineral density.

Because of these side effects, hormonal therapies utilizing a GnRH compound typically include administration of an estrogen compound and/or a progestin compound; so-called "add-back" hormonal therapy. The progestin compound is administered for some portion of each month to induce shedding of the endometrial lining or continuously in order to protect the female from endometrial hyperplasia. For example, in U.S. Pat. No. 5,340,585 administration of a GnRH compound for treating benign gynecological disorders is described. The GnRH compound is co-administered with an estrogenic compound to minimize the side effects that result from the reduction in estradiol levels by the GnRH compound. The composition, however, is specifically limited to use in women in whom the risk of endometrial stimulation is minimized or absent, such as women who have had a hysterectomy, those using a progesterone releasing intrauterine device, or those taking a separate progestin.

Another example of hormonal therapy based on administration of a GnRH agonist has been proposed to ameliorate symptoms associated with premenstrual syndrome (Mortola, J. F., et al., *J. Clin. Endocrin. Metab.,*72:252A–252F (1991)). The therapy includes co-administration of an estrogen and co-administration for a portion of the 28 day treatment period, a progestin, medroxyprogesterone acetate.

The prior art also reports parenteral administration of GnRH compounds with co-administration of an oral estrogen (Sugimoto, A. et al., *Fertility and Sterility,* 60(4):672 (1993)). A progestin, medroxyprogesterone acetate, was added for 14 days of each calendar month for endometrial protection in hirsute women, but was omitted in other test patients to prevent disease-specific symptoms associated with progestins. In the patients receiving unopposed estrogen, that is in the women treated with a GnRH and estrogen in the absence of a progestin, 4 of the 12 females had simple endometrial hyperplasia.

There remains a need in the art for a hormonal therapy for treatment of benign gynecological disorders that excludes a progestin, to avoid the conditions and symptoms, such as increased incidence of breast cancer, associated with this hormone. However, the prior art suggests that endometrial hyperplasia results from administration of unopposed estrogen. Thus, while the prior art recognizes the use of GnRH compounds for treatment of benign gynecological disorders, prior art compositions either included a progestin as an "add-back" compound or limited the treatment to women not at risk for endometrial stimulation, i.e., women receiving an exogenously supplied progestin on a regular or periodic basis or women who have had a hysterectomy.

SUMMARY OF THE INVENTION

Accordingly, it is an object of the invention to provide a method of treating benign gynecological disorders by administering a composition comprised of a GnRH compound and an estrogenic compound and, optionally, an androgenic compound, in the absence of a co-administered or sequentially administered progestin.

It is another object of the invention to provide a method of preventing pregnancy, i.e., a method of contraception, by administering a composition comprised of a GnRH compound and an estrogenic compound and, optionally, an androgenic compound, in the absence of a co-administered or sequentially administered progestin.

The present invention is based on the finding that women who are not receiving an exogenously supplied progestin can be treated with a GnRH compound combined with an estrogenic compound and, optionally, an androgenic compound for an extended period of time (i.e., 6 to 12 months or more) with no increase in the risk of endometrial hyperplasia. That is, treatment of a benign gynecological disorder with a composition comprised of a GnRH compound and an estrogenic compound and, optionally, an androgenic compound need not be accompanied by simultaneous administration of an exogenously supplied progestin in order to prevent endometrial hyperplasia. Similarly, administration of a GnRH compound and an estrogenic compound and, optionally, an androgenic compound for contraception need not be in conjunction with administration of an exogenously supplied progestin in order to prevent endometrial hyperplasia.

Accordingly, in one aspect, the invention includes an improvement in a method of treating benign gynecological disorders in a female. In the method, co-administration of a GnRH compound in an amount effective to suppress ovarian estrogen and progesterone production, and an estrogenic compound along with, optionally an androgen, in an amount effective to prevent signs and symptoms of estrogen deficiency and androgen deficiency, is extended to a female patient population of premenopausal women who are not receiving an exogenously supplied progestin on a regular or periodic basis and who do not have a history of endometrial hyperplasia, without a significant increase in the risk of endometrial hyperplasia relative to the patient population of women who are receiving an exogenously supplied progestin.

In one embodiment, the GnRH compound is a GnRH peptide agonist, and exemplary GnRH agonist compounds include deslorelin, leuprolide, nafarelin, goserelin, decapeptyl, buserelin, histrelin, gonadorelin, and analogs thereof. Exemplary GnRH antagonist compounds include azaline B, abarelix, cetrorelix, degarelix, and analogs thereof.

In another embodiment, the GnRH agonist is administered by an intranasal route. The co-administered estrogenic compound, in one embodiment, is also administered intranasally, and in another embodiment, it is administered transdermally. A preferred estrogenic compound is 17β-estradiol. When administered transdermally, 17-β-estradiol is administered at a daily dose between about 0.025 mg and about 0.1 mg.

As noted above, the composition can optionally include an androgen. Thus, in one embodiment, the method includes co-administering an androgenic compound such as testosterone. The androgen can be administered intranasally or by a transdermal route with the estrogenic compound. When the androgen is testosterone it can be administered at a daily dose sufficient to increase the average serum testosterone level over 24 hours to the premenopausal range of about 15 ng/dL to 80 ng/dL.

In another embodiment, the GnRH agonist and the estrogenic compound are co-administered intranasally, in an aerosol spray containing a daily spray volume between about 30 and 200 μL, and between about 0.15 mg and 0.6 mg of 17β-estradiol. In yet another embodiment, the intranasal administration further includes co-administering testosterone by an intranasal route, in an aerosol spray containing a daily spray volume between 30 and 200 μL, and between 0.15 mg and 0.6 mg of 17β-estradiol and between 0.15 mg and about 1 mg of testosterone.

In another aspect, the invention includes a method of treating benign gynecological disorders in a patient population composed of premenopausal women who do not have a history of endometrial hyperplasia, and who are not receiving an exogenously supplied progestin on a regular or periodic basis. The method includes administering by daily intranasal administration, over an extended period of time between 6 and 12 months, a formulation containing a GnRH compound, in an amount effective to suppress ovarian estrogen and progesterone production, and an estrogenic compound and optionally an androgen, in an amount effective to prevent signs and symptoms of estrogen deficiency and androgen deficiency over a time period of between about 6 and 12 months.

In one embodiment, the nasal formulation is an aqueous formulation, and said administering is effective to deliver a daily spray volume between 30 and 200 μL.

In another embodiment, the spray volume administered includes between 0.15 and 0.6 mg of 17β-estradiol. In yet another embodiment, the spray volume further includes testosterone in an amount between 0.15 mg and 1 mg.

The spray volume can further include, in another embodiment, a cyclodextrin, such as 2-hydroxypropyl-β-cyclodextrin. Preferably, the 2-hydroxypropyl-β-cyclodextrin, when present, is present in a mole ratio of cyclodextrin to total steroid of between 1:1 and 3:1.

The nasal formulation can also take the form of an aerosolizable dry powder, as will be further described below. In one embodiment, the dry powder also includes testosterone, in a mole ratio of estrogenic compound: testosterone of between 1:1 and 1:2.

In another aspect, the invention includes an improvement in a method for contraception. The improvement comprises extending the contraceptive method of administering a GnRH compound and an estrogenic compound to women who are not receiving an exogenously supplied progestin on a regular or periodic basis. The method includes administering by daily intranasal administration, over an extended period of time between about 6 and 12 months, a formulation containing a GnRH compound, in an amount effective to suppress ovarian estrogen and progesterone production, and an estrogenic compound, and optionally an androgen, in an amount effective to prevent signs and symptoms of estrogen deficiency and androgen deficiency over a time period of between about 6 and 12 months.

These and other objects and features of the invention will be more fully appreciated when the following detailed description of the invention is read in conjunction with the accompanying drawings and examples.

DETAILED DESCRIPTION OF THE INVENTION

I. Definitions

Figure 1A:
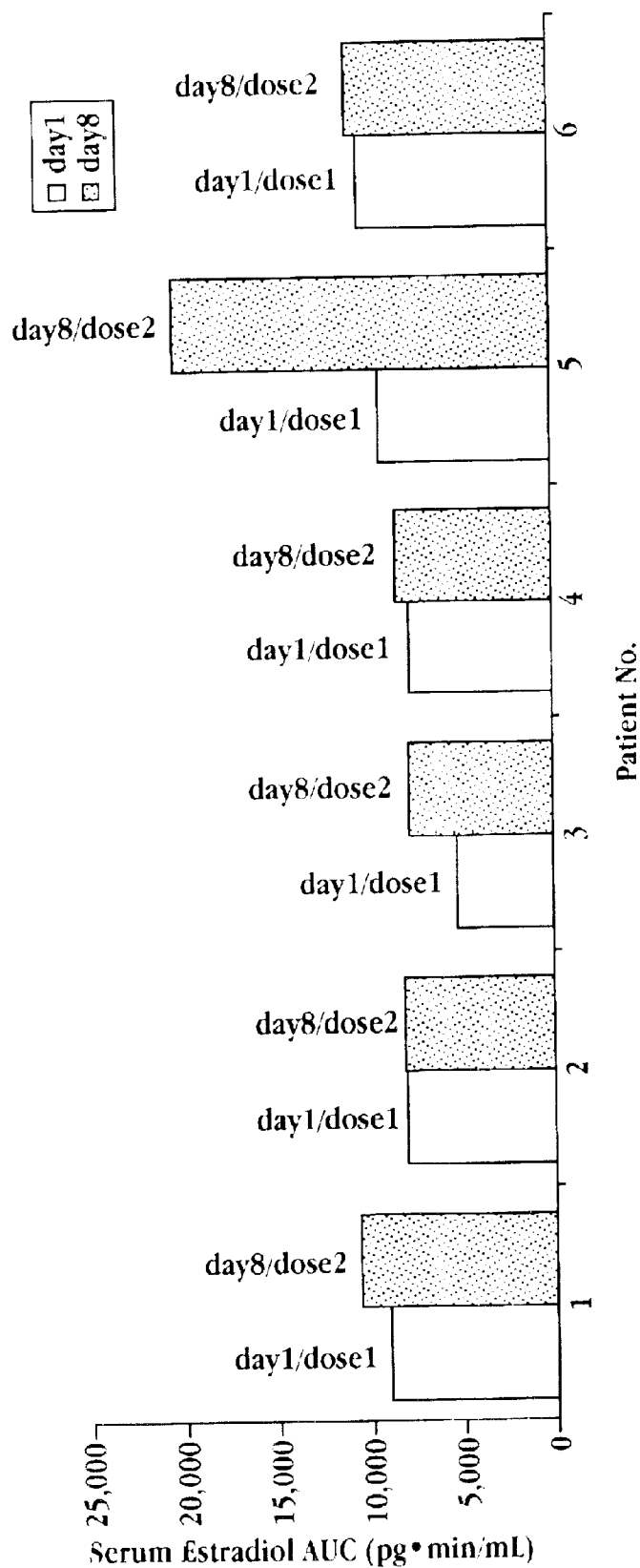
FIGS. 1A and 1B are bar graphs showing the cumulative area under the curve from 0 to 360 minutes in pg·min/mL of serum estradiol (FIG. 1A) and in ng·min/dL of serum testosterone (FIG. 1B) for six patients treated with an intranasal preparation comprised of the GnRH compound deslorelin, estradiol, and testosterone. The preparation was administered twice (days 1 and 8), one week apart.

The phrase "regular basis" intends an on-going, and predictably scheduled action. A "regular basis" can be periodic when the action is not necessarily continuous, but the action occurs at a period that is predictable or scheduled in an on-going fashion.

A "periodic basis" intends an action that is intermittent and predictably scheduled.

An "extended time period" intends a period of more than about 4 months, preferably more than about 6 months.

The term "premenopausal" refers to the period corresponding to a woman's reproductive years defined as the time between onset of menses (menarche) and the final episode of menstrual bleeding (menopause).

The phrase "amount effective to prevent signs and symptoms of estrogen deficiency" refers to a dose of a therapeutic compound that inhibits or minimizes clinically-recognized markers of estrogen deficiency, including but not limited to symptoms typically associated with menopause, such as vasomotor instability, bone loss, and/or urogenital atrophy.

The phrase "amount effective to prevent signs and symptoms of androgen deficiency" intends a dose of a therapeutic compound that inhibits or minimizes clinically-recognized indicators of androgen deficiency, and in particular the clinical indicators of testosterone deficiency such as bone loss and decreased libido. Such signs and symptoms typically overlap with or are a subset of the signs and symptoms of estrogen deficiency.

The terms "progestin" and "progestogen" are used interchangeably.

The term "GnRH compound" as used herein intends peptide and non-peptide GnRH analogs, and includes agonists and antagonists. Exemplary non-peptide analogs are described, for example, in U.S. Pat. No. 6,346,534. Peptide analogs are widely reported in the literature and examples are provided herein.

II. Method of Treatment

As noted above, in one aspect the invention includes a method of treating a benign gynecological disorder in a woman by administration of a GnRH compound in combination with an estrogenic compound and optionally an androgenic compound. In this section, each component in the composition and exemplary routes of administration will be described.

A1. Composition Components: GnRH Compound

The composition for use in the method of the invention comprises a GnRH compound. Native GnRH is a decapeptide comprised of naturally-occurring amino acids having the L-configuration, except for the achiral amino acid glycine. The sequence of GnRH is (pyro)Glu-His-Trp-Ser-Tyr-Gly-Leu-Arg-Pro-Gly-NH$_2$ (SEQ ID NO:1). A large number of analogs of this natural peptide have been prepared and are effective to inhibit the release and/or the action of GnRH. Analogs having agonist and antagonist activity have been described, and as used herein, the term "a GnRH compound" or "GnRH compounds" intends agonists and antagonists, synthetically prepared or naturally-occurring, peptides and non-peptide compounds alike. The following description focuses in particular on GnRH agonists, however, it will be appreciated that native GnRH, GnRH antagonists, such as azaline B, abarelix, cetrorelix, and degarelix, and other GnRH analogs are also suitable for use in the composition and method of treatment. Further, the following discussion focuses on peptide analogs, however, it will be appreciated that non-peptide compounds, such as those disclosed in U.S. Pat. No. 6,346,534, are also contemplated.

GnRH agonists are compounds that work in two phases. The first phase stimulates the ovaries to produce more estradiol. During the second phase, the messenger hormones that control the ovaries are no longer produced, resulting in a drop in estrogen. An exemplary agonist is obtained by changing the 6-position residue in the naturally-occurring GnRH from Gly to a D-amino acid, to give a GnRH analog having a sequence (pyro)Glu-His-Trp-Ser-Tyr-X-Leu-Arg-Pro-Gly-NH$_2$ (SEQ ID NO:2), where X represents an amino acid in the D-configuration. When X is D-Leu the analog is known as Lupron™ and is commercially available from TAP Pharmaceuticals (Lake Forest, Ill.). Agonists often have the N-terminus prolyl modified with an n-ethylamide addition. For example, the agonist deslorelin is (pyro)Pro-His-Trp-Ser-Tyr-DTrp-Leu-Arg-Pro-ethylamide (SEQ ID NO:3). Another exemplary analog is where the 6-position residue is D-Ala to give a peptide having the following sequence: (pyro)Glu-His-Trp-Ser-Tyr-D-Ala-Leu-Arg-Pro-Gly-NH$_2$ (SEQ ID NO:4; U.S. Pat. No. 4,072,668). Another exemplary agonist is obtained by eliminating the Gly-NH$_2$ in position 10 to give a nonapeptide as an alkyl, cycloalkyl, or fluoroalkylamide, or by replacing Gly-NH$_2$ by an a-azaglycine amide. Modifications to the naturally-occurring GnRH sequence at positions 1 and 2 are also possible. A number of GnRH agonists are described in the art, many of which are commercially available, and include deslorelin, leuprolide, nafarelin, goserelin, decapeptyl, buserelin, histrelin, and gonadorelin, and analogs thereof.

The amount of GnRH compound effective to achieve the desired suppression of ovarian estrogen production may readily be determined with respect to any given GnRH compound and for any given mammal. The dose range depends upon the particular GnRH compound used and may also depend upon patient characteristics, such as age and weight. Further, the effective amount of GnRH compound also depends upon route of administration. Determination of an effective dose range after consideration of these factors is routine for those of skill in the art.

By way of example of a specific formulation, the amount of GnRH compound when the GnRH compound is deslorelin in a daily nasal spray formulation with a volume between about 30 to 200 µL can deliver a daily dose of GnRH compound of between about 0.025 mg to about 1.5 mg, more preferably from about 0.025 mg to about 0.1 mg. It will be appreciated that the daily spray volume can be administered in one, two, or more separate deliveries to achieve the desired total daily spray volume. It will further be appreciated that the spray volume and the amount of GnRH compound in the nasal formulation are both individually adjustable to achieve the desired daily dosage.

A2. Composition Components: Estrogenic Compound

A second component in the composition for use in the method of the invention is an effective amount of an estrogenic compound. The estrogenic compound is effective to prevent symptoms and signs of estrogen deficiency including bone loss, vaginal atrophy, and hot flashes.

The estrogenic compound can be a single-component natural or synthetic estrogen composition, or a combination of such compounds. As used herein, the term "estrogenic compound" refers to both natural and synthetic materials having activity to mitigate the signs and symptoms of estrogen deficiency. Natural and synthetic estrogenic compositions which can be used according to the invention described herein include natural estrogenic hormones and congeners, including but not limited to estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol, and estrone potassium sulfate. Equine estrogens, such as equilelinin, equilelinin sulfate, and estetrol, and synthetic steroids combining estrogenic, androgenic, and progestogenic properties such as tibolone may also be employed.

Typical dose ranges for estrogenic compounds depend on the compound and on the characteristics of the patient. For an adult human female patient treated with a transdermal 17β-estradiol preparation, a typical dose range is one that maintains a serum level of estradiol of about 25 to about 140 pg/mL, more preferably between about 30 to about 50 pg/mL. A specific example of a composition containing an estrogenic compound is one comprised of a GnRH agonist and 17-β-estradiol. The two compounds, along with other optional excipients or an androgenic compound, are formulated for transdermal or intranasal delivery. In a transdermal formulation, a preferred daily dosage range for 17-β-estradiol is between about 0.025 mg and 0.1 mg. For an intranasal preparation, a preferred daily dosage range for 17-β-estradiol is between about 0.15 mg and 0.6 mg.

As discussed below, the estrogenic compound is preferably co-administered from the same delivery vehicle or via the same route as the GnRH compound. However, delivery of the estrogenic compound can be from a different vehicle and/or by a different route than the GnRH compound, and some examples of such "mixed modes" of administration are provided below. As can be appreciated, the composition comprised of a GnRH compound and an estrogenic compound suppresses gonadotropin activity while providing a replacement of estrogen to minimize or eliminate the side effects associated with suppression of gonadotropin activity.

A3. Composition Components: Androgenic Compound

The composition comprised of a GnRH compound and an estrogenic compound can optionally include an androgenic compound. When present in the composition, the androgenic compound is in an amount effective to increase a patient's androgen level to a level not exceeding a "normal" pre-menopausal level, and in particular in concert with the estrogenic composition to maintain bone mineral density. Such "normal" androgen levels are on the order of about 15 ng/dL to about 80 ng/dL for testosterone.

Suitable androgenic compounds for use in the composition include but are not limited to testosterone, androstenedione, dihydrotestosterone, testosterone propionate, testosterone enanthate, testosterone cypionate, methyltestosterone, danazol, dromostanolone propionate, ethylestrenol, methandriol, nandrolone decanoate, nandrolone phenpropionate, oxandrolone, oxymethalone, and stanozolol.

Typical dose ranges for androgenic hormones depend upon the choice of compound and the individual patient. For an adult human female administered testosterone, typical doses are administered to provide average serum levels of testosterone of from about 15 ng/dL to about 80 ng/dL, and preferably about 40 ng/dL to about 60 ng/dL. A specific example of a composition containing an androgenic compound is one comprised of a GnRH agonist and 17-β-estradiol and testosterone. The compounds, along with other optional excipients, are formulated for delivery transdermally or intranasally. For an intranasal preparation, a typical daily dose of testosterone can range from about 0.15 mg to about 1 mg.

B. Exemplary Modes of Administration

As noted above, the compositions described herein are beneficial for use in female contraception and/or in the treatment of benign gynecological disorders. In general, the compositions can be administered by any vehicle or route that achieves efficacious therapy. Parenteral (e.g., non-gastrointestinal, such as subcutaneous, intramuscular, intravenous), transdermal, pulmonary, mucosal (nasal, vaginal, rectal, buccal) routes of delivery are contemplated and preparation of suitable dosage forms can be prepared by methods well-known in the pharmaceutical art, for example, as described in *Remington's Pharmaceutical Sciences*, $17^{th}$ ed., Mack Publishing Co., Easton, Pa. (1985). Some exemplary formulations for various routes of administration are discussed below.

For example, in one embodiment it is contemplated that the composition is administered mucosally by contacting the composition in a suitable dosage form with mucosal tissue of the vagina, nose, rectum, or mouth. In a preferred embodiment, the composition is administered via the nasal mucosa, e.g., intranasally. The nasal mucosa provides a useful anatomical site for systemic delivery. The nasal tissue is highly vascularized, providing an attractive site for rapid and efficient absorption. The adult nasal cavity has a capacity of around 20 mL, with a large surface area of approximately 180 $cm^2$ for drug absorption, due in part to the microvilli present along the psuedostratified columnar epithelial cells of the nasal mucosa.

A nasal preparation comprised of the composition described above can take a variety of forms for administration in nasal drops, nasal spray, gel, ointment, cream, powder or suspension, using a dispenser or other device as needed. A variety of dispensers and delivery vehicles are known in the art, including single-dose ampoules, atomizers, nebulizers, pumps, nasal pads, nasal sponges, nasal capsules, and the like.

More generally, the preparation can take a solid, semi-solid, or liquid form. In the case of a solid form, the components may be mixed together by blending, tumble mixing, freeze-drying, solvent evaporation, co-grinding, spray-drying, and other techniques known in the art. Such solid state preparations preferably provide a dry, powdery composition with particles in the range of between about 20 to about 500 microns, more preferably from 50 to 250 microns, for administration intranasally.

A semi-solid preparation suitable for intranasal administration can take the form of an aqueous or oil-based gel or ointment. For example, the components described above can be mixed with microspheres of starch, gelatin, collagen, dextran, polylactide, polyglycolide, or other similar materials that are capable of forming hydrophilic gels. The microspheres can be loaded with drug, and upon administration form a gel that adheres to the nasal mucosa.

In a preferred embodiment, the nasal preparation is in liquid form, which can include an aqueous solution, an aqueous suspension, an oil solution, an oil suspension, or an emulsion, depending on the physicochemical properties of the composition components. The liquid preparation is administered as a nasal spray or as nasa drops, using devices known in the art, including nebulizers capable of delivering selected volumes of formulations as liquid-droplet aerosols. For example, a commercially available spray pump with a delivery volume of 50 μL or 100 μL is available from, for example, Valois (Congers, N.Y.) with spray tips in adult size and pediatric size. In one embodiment, the composition comprised of a GnRH agonist and an estrogenic compound are co-administered intranasally via an aerosol spray in a daily volume of between about 10 to 500 μL, more preferably between about 30 to about 200 μL.

The liquid preparation can be produced by known procedures. For example, an aqueous preparation for nasal administration can be produced by dissolving, suspending, or emulsifying the polypeptide and the steroid compounds in water, buffer, or other aqueous medium, or in a oleaginous base, such as a pharmaceutically-acceptable oil like olive oil, lanoline, silicone oil, glycerine fatty acids, and the like.

It will be appreciated that excipients necessary for formulation, stability, and/or bioavailability can be included in the preparation. Exemplary excipients include sugars (glucose, sorbitol, mannitol, sucrose), uptake enhancers (chitosan), thickening agents and stability enhancers (celluloses, polyvinyl pyrrolidone, starch, etc.), buffers, preservatives, and/or acids and bases to adjust the pH.

In a preferred embodiment, an absorption promoting component is included. Exemplary absorption promoting components include surfactant acids, such as cholic acid, glycocholic acid, taurocholic acid, and other cholic acid derivatives, chitosan, and cyclodextrins. In a preferred embodiment, a cyclodextrin is included in the preparation. Cyclodextrins are cyclic oligosaccharides of α-D-glucopyranose and can be formed by the catalytic cyclization of starch. Due to a lack of free rotation about the bonds connecting the glycopyranose units, cyclodextrins are toroidal or cone shaped, rather than cylindrical. The cyclodextrins have a relatively hydrophobic central cavity and a hydrophilic outer surface. The hydrophobic cage-like structure of cyclodextrins has the ability to entrap a variety of guest compounds to form host-guest complexes in the solid state and in solution. These complexes are often termed inclusion complexes and the guest compounds are released from the inclusion site.

The most common cyclodextrins are α-, β-, and γ-cyclodextrin, which consist of six, seven, or eight glucopyranose units, respectively. Cyclodextrins containing nine, ten, eleven, twelve, and thirteen glucopyranose units are designated δ-, ε-, ξ-, η-, and θ-cyclodextrin, respectively. Characteristics of α-, β-, γ-, and δ-cyclodextrin are shown in Table 1.

Derivatives formed by reaction with the hydroxyl groups lining the upper and lower ridges of the toroid are readily prepared and offer a means of modifying the physicochemical properties of the parent cyclodextrins. The parent cyclodextrins, and in particular β-cyclodextrin, have limited aqueous solubility. Substitution of the hydroxyl groups, even with hydrophobic moieties such as methoxy and ethoxy moieties, typically increases solubility. Since each cyclodextrin hydroxyl group differs in chemical reactivity, reaction with a modifying moiety usually produces an amorphous mixture of positional and optical isomers. The aggregate substitution that occurs is described by a term called the degree of substitution. For example, a 2-hydroxypropyl-β-cyclodextrin with a degree of substitution of five would be composed of a distribution of isomers of 2-hydroxypropyl-β-cyclodextrin in which the average number of hydroxypropyl groups per 2-hydroxypropyl-β-cyclodextrin molecule is five. Degree of substitution can be determined by mass spectrometry or nuclear magnetic resonance spectroscopy. These methods do not give information as to the exact location of the substituents (C1, C2, C3, etc.) or the distribution of the substituents on the cyclodextrin molecule (mono, di, tri, poly). Theoretically, the maximum degree of substitution is 18 for α-cyclodextrin, 21 for β-cyclodextrin, and 24 for γ-cyclodextrin, however, substituents with hydroxyl groups present the possibility for additional hydroxylalkylations.

The cyclodextrin used in the present invention is preferably an α-, β-, or γ-cyclodextrin. The cyclodextrin is selected for use depending on which cyclodextrin binds the guest compounds and yields the desired bioavailability. In a preferred embodiment, a derivative of a cyclodextrin is selected, and derivatives such as hydroxypropyl, dimethyl, and trimethyl substituted cyclodextrins are contemplated, as are cyclodextrins linked with sugar molecules, sulfonated cyclodextrins, carboxylated cyclodextrins, and amino derivatives such as diethylamino cyclodextrins. In a preferred embodiment, the cyclodextrin is a β-cyclodextrin, and in a more preferred embodiment, the cyclodextrin is 2-hydroxypropyl-β-cyclodextrin. In yet another embodiment, the 2-hydroxypropyl-β-cyclodextrin has a degree of substitution between 2 and 8, more preferably between 4 and 8, most preferably between 5 and 8.

In a study performed in support of the invention, an intranasal formulation comprised of the GnRH compound deslorelin and of estradiol, testosterone, and cyclodextrin was prepared, as described in Example 1 and further discussed below.

Another exemplary mode of administration suitable for the method of the invention is an intravaginal device, such as an intravaginal ring or a vaginal thin-film laminate. Vaginal rings are well-known in the art (see for example Duncan et al., *Silicone Based Release Systems*, in POLYMERS IN MEDICINE AND SURGERY, Kronenthal et al. Eds., Plenum, N.Y., 1975, p. 205; U.S. Pat. Nos. 4,012,496; 5,869,081) and

TABLE 1

| Cyclodextrin Characteristics | | | | |
|---|---|---|---|---|
| | α-cyclodextrin | β-cyclodextrin | γ-cyclodextrin | δ-cyclodextrin |
| no. of glucopyranose units | 6 | 7 | 8 | 9 |
| molecular weight (Daltons) | 972 | 1135 | 1297 | 1459 |
| central cavity diameter (Å) | 4.7–5.3 | 6.0–6.5 | 7.5–8.3 | 10.3–11.2 |
| water solubility (at 25° C., g/100 mL) | 14.5 | 1.85 | 23.2 | 8.19 | are made by polymerizing in a simple mold a mixture of the drug dispersion and a suitable polymer, such as silicone rubber. The ring or device is inserted into the vaginal cavity and retained there for a desired period of time for administration of the compounds incorporated into the device. Vaginal devices are described in LONG-ACTINGCONTRACEPTIVEDELIVERYSYSTEMS, Zatuchni, G., L., et al. Eds., 1984, and the particular chapters by Jackanicz, T. M., "Vaginal Ring Steroid-Releasing Systems, p. 201–212; by Diczfalusy & Landgren, "Some Pharmacokinetic and Pharmacodynamic Properties of Vaginal Delivery Systems that Release Small Amounts of Progestogens at a Near Zero-Order Rate", p. 213–227; and by Roy & Mishell, "Vaginal Ring Clinical Studies: Update", p. 581–594, are incorporated by reference herein.

Another exemplary mode of administration is transdermal. Transdermal administration is one approach to achieving a constant blood level of drug in a patient for a period of time. Transdermal administration offers, in addition to the benefit of a more constant blood level, other benefits such as a more efficient utilization of the drug, the potential for localized, site specific delivery, and less frequent administration (Baker, R. W., CONTROLLEDRELEASE OFBIOLOGICALLYACTIVEAGENTS, John Wiley and Sons, New York, (1987) p. 5–10). More efficient utilization of the drug is an important benefit, since often less drug, when administered in a controlled release manner, is required to produce a given duration of effect than when administered by another route. This is particularly true if the half-life of the drug is short compared with the desired treatment period. Since the drug is utilized more efficiently, a considerably lower dose may be required, depending on the drug half-life and the desired time of treatment.

Transdermal delivery devices, also referred to as transdermal patches, have been widely described (see, for example, Baker, R. W., Id.). The transdermal device can be a simple adhesive matrix type device with the active agents incorporated into the adhesive layer, or a more complicated device with one or more drug reservoirs defined by an impermeable backing layer and a retaining membrane. Design of the device and selection of suitable materials is readily accomplished by those of skill in the art. An exemplary device for use in the present invention is one designed to administer to a patient a dose of GnRH and an estrogenic compound and, optionally, an androgenic compound in an amount sufficient to treat a benign gynecological disorder and/or achieve contraception.

The present invention contemplates administration of the GnRH compound and the estrogenic compound, optionally containing an androgen, as a single composition by a single route of administration. For example, a dry powder comprised of the GnRH compound, the estrogenic compound, and, optionally, an androgen, and any desired excipients or enhancers, such as cyclodextrin, are mixed into a dosage form suitable for co-administration intranasally in the form of a dry aerosol. Or, for example, the same compounds are formulated into a liquid preparation for intranasal administration as a spray. Or, for example, the same compounds are incorporated into a transdermal device for co-administration of the GnRH, estrogenic compound, and the androgenic compound, if present, via the skin.

The invention further contemplates administration of the GnRH compound and the estrogenic compound, optionally containing an androgenic compound, in the form of two or more compositions for administration by two or more routes of administration. For example, the GnRH compound can be formulated into an intranasal preparation, and the estrogenic compound and, optionally, the androgenic compound can be formulated into a transdermal device. The two formulations are administered to a patient for treatment of a benign gynecological disorder or for contraception. That is, the GnRH is administered intranasally as needed to achieve the desired daily dose, and the estrogenic compound and, optionally, the androgenic compound is administered transdermally. It will be appreciated that the androgenic compound can be included in either formulation, preferably in the transdermal device, or administered as a separate, third composition by any suitable route. Other 'mixed modes' of administration will be readily apparent to those of skill in the art.

C. In vivo Treatment Method

As noted above, the invention provides for an improvement in a method of treating benign gynecological disorders and for an improvement in a method of contraception, where a GnRH compound and an estrogenic compound and, optionally, an androgenic compound are administered to women in conjunction with an exogenously supplied progestin on a regular or periodic basis. The improvement consists of administering the GnRH compound and the estrogenic compound and, optionally, an androgenic compound, to women who are not receiving an exogenously supplied progestin on a regular or periodic basis. As will be described below, the improved method of treatment finds basis in the discovery that an exogenously supplied progestin is not required on a regular or periodic basis to prevent endometrial hyperplasia.

Thus, in a preferred embodiment, the improved method described herein extends treatment of benign gynecological disorders by administration of a GnRH compound and an estrogenic compound and, optionally, an androgenic compound to women not receiving an exogenously supplied progestin on a regular or periodic basis. However, it is to be understood that women treated in accord with the invention may be treated with an exogenously supplied progestin on an intermittent basis. That is, a physician may prescribe an occasional progestin to induce shedding of the endometrium or to preserve efficacy of the GnRH-estrogenic (and optionally androgenic) composition. Typically, the GnRH compound and the estrogenic compound and, optional androgenic compound are administered for an extended period of time, e.g., longer than about 6 months to 12 months, and, if, for example, shedding of the endometrium is desired, a progestin can be taken for a defined interval of time. Thus, the invention further contemplates treatment of a benign gynecological disorder or contraception by administration of the GnRH compound and the estrogenic compound and optional androgenic compound, where a progestin is prescribed on an intermittent, i.e., irregular, non-predictable, basis.

In studies performed in support of the invention, the GnRH compound deslorelin was administered intranasally to patients, both in the presence and absence of estradiol and/or testosterone. These studies will now be described.

Intranasal administration of deslorelin alone is described in Example 2. The objective of this study was to determine an appropriate dose of the GnRH compound deslorelin effective to control the heavy bleeding secondary to uterine leiomyomata (fibroids). As described in Example 2, female patients were treated with deslorelin administered daily via intranasal delivery, at a dose of 0.5 mg, 1.0 mg, or 2.0 mg. The compound was administered using a commercially available nasal sprayer that delivered a 50 µL spray volume. The daily dose was administered by application of 50 µL to each nostril once per day, for a total daily spray volume of 100 μL. During the 12 week treatment period the patients kept daily bleeding calendars and underwent clinical assessments at scheduled intervals. Clinical assessments included grading of nasal irritation (Table 3A), determination of uterus size (Table 3B), and serum hormonal levels (Table 3C). These clinical data are presented in the indicated tables in Example 2, along with the bleeding scores (Table 3D)

With respect to nasal irritation, the data (Table 3A in Example 2) indicate that subjects experienced none or slight irritation at deslorelin dosages of 0.5 mg and 1 mg. Some of the subjects treated with a deslorelin dose of 2 mg experienced more frequent irritation.

Table 3B in Example 2 also shows a reduction in uterine volume (calculated from ultrasound determined dimensions), with the reduction directly correlating to deslorelin dose.

Serum levels of estradiol, progesterone, and testosterone are shown in Table 3C in Example 2. Reduction in estradiol levels was progressive and dose dependent over the 12 week period. Progesterone levels followed a similar pattern with progressive suppression with higher dose and longer time. Testosterone levels are also similar.

With respect to bleeding scores (Table 3D in Example 2), the patients treated with the GnRH compound had a marked improvement in their bleeding score at the end of the three month study.

In summary, all tested doses were partially or completely effective, as evidenced by a reduction of bleeding, and uterine size. This effect correlates with a reduction of estrogen and progesterone. Based on the bleeding scores, a 1.0 mg dose appears to offer a slight advantage compared with the 0.5 mg dose. Uterine size and rates of change of estrogen and testosterone levels are clearly dose related over the range studied.

Another study performed in support of the invention is described in Example 3. In this study, the GnRH compound deslorelin, estradiol, and testosterone were co-administered as an "all-in-one" nasal spray to oophorectomized women. Each woman was treated with 50 μL of a nasal spray preparation, prepared as described in Example 1, delivered as a single dose on two occasions separated by one week. The 50 μL dose delivered 1 mg deslorelin, 50 μg estradiol, and 250 μg testosterone. The estradiol and testosterone were in the form of a water-soluble complex with cyclodextrin. Blood samples were collected prior to and after dosing on each test day for quantitation of serum estradiol and testosterone levels. The results are presented in FIGS. 1A and 1B.

Figure 1B:
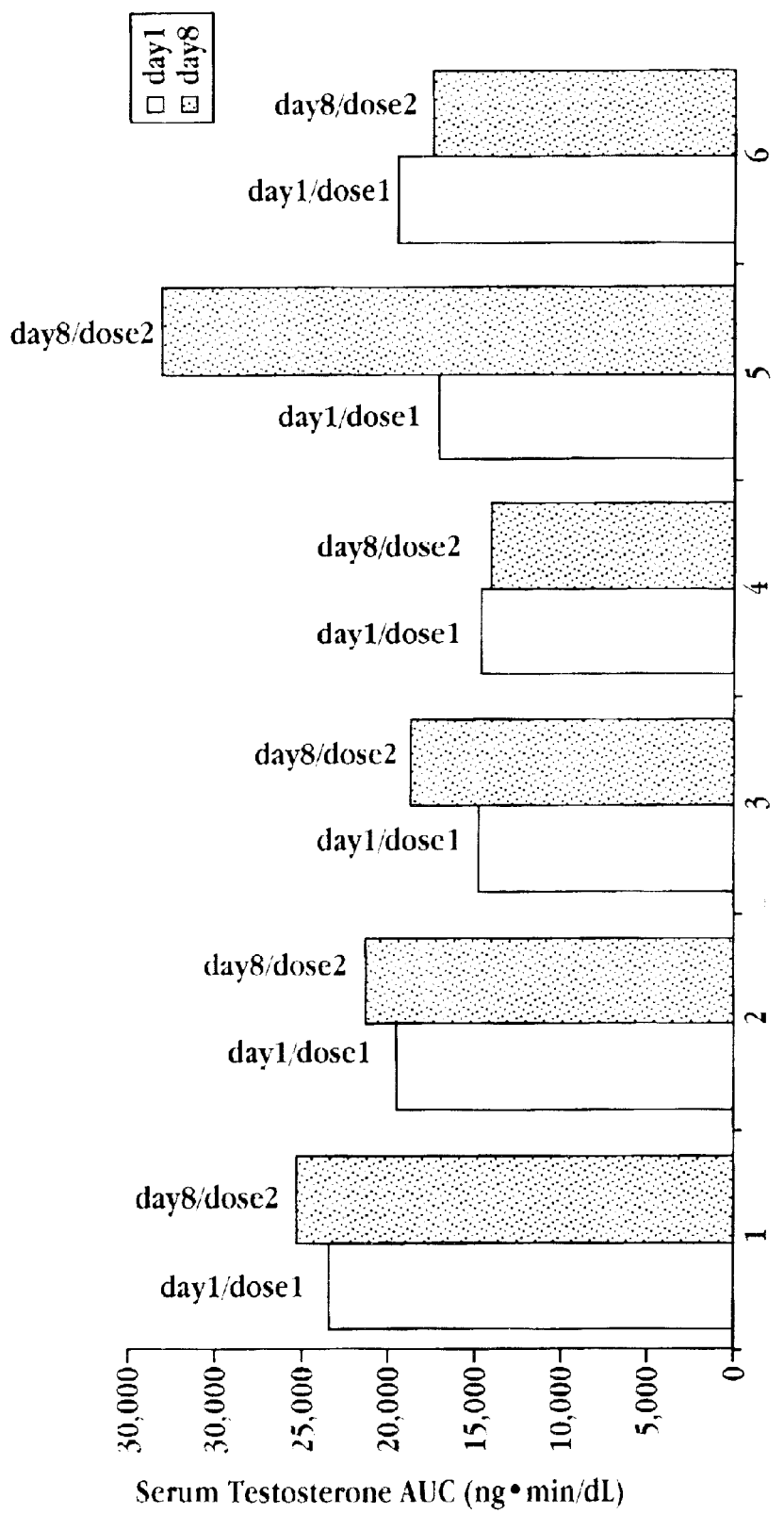

FIG. 1A is a bar graph showing the cumulative area under the curve (AUC) from 0 to 360 minutes for serum estradiol, in pg*min/mL, for each of the six patients. FIG. 1B is a similar graph for testosterone. The hormone levels on day 1 and day 8, corresponding to dose 1 and dose 2, are shown as a separate bar for each patient. Comparison of the AUC of each patient shows that uptake of the compounds in the nasal preparation is relatively uniform, with variations between patients likely due to varying extent of metabolic conversion during nasal mucosa absorption. Importantly, the data also show that significant absorption of estradiol and testosterone occurs in the presence of the GnRH compound.

In this study, the estrogenic compound estradiol and testosterone were present in the formulation at a molar ratio of 1:5 (MW estradiol=272.4 g/mol; MW testosterone=288.4 g/mol). The ratio of these two hormones can range from between about 1:1 to 1:5, and more preferably range from about 1:1 to 1:3, and most preferably from 1:1 to 1:2.

Example 4 describes a study performed in support of the invention where the nasal preparation is similar to that of Example 1, comprised of a GnRH compound, estradiol, and testosterone, was administered to healthy, premenopausal women. Three doses of the GnRH compound deslorelin were tested, 0.5 mg, 1.0 mg, and 2.0 mg. The nasal preparation was administered using a conventional metered nasal spray delivery device. The subjects received two 50 μL sprays, one in each nostril, daily for four weeks. Blood samples were collected prior to drug administration on day 1 of the study, and then at regular intervals throughout day 1. Thereafter, blood samples were collected weekly, until day 29, when blood was collected at scheduled intervals throughout the day. Serum deslorelin, estradiol, testosterone, and progesterone were quantified, and the results are shown in Tables 4A through 4C, below in Example 4.

The degree of induced ovarian suppression is evident from the serum estradiol and progesterone levels (Tables 4A–4C). Serum levels of estradiol on day 29 varied from 14 to 103 pg/mL. Progesterone levels were generally less than 80 ng/dL during the treatment interval indicating that women were anovulatory during the treatment.

In one embodiment, the intranasal dose of the estrogenic compound, and the optional androgen if present, achieve a transientserum level outside the serum estradiol level of between about 25 pg/mL to about 140 pg/mL that is typically reported in the literature with a 50 μg/day transdermal patch. Although the serum hormone levels resulting from intranasal delivery of the hormone(s) are transiently outside this range a similar beneficial effect is achieved. That is, the biological effect(s) resulting from intranasal delivery of an estrogenic compound, and the optional androgenic compound, is similar to the biological effect associated with a serum estradiol level of between about 25 pg/mL to about 140 pg/mL even though the actual transient serum level may be outside this range. Thus, in one embodiment, the invention contemplates administration of an estrogenic compound and an optional androgenic compound in an amount sufficient to achieve the beneficial biological effects that are associated with an steady estradiol serum level of between about 25 pg/mL to about 140 pg/mL, more preferably between about 30 pg/mL to about 100 pg/mL, most preferably between about 30 pg/mL to about 50 pg/mL. In intranasal formulations where the optional androgenic compound is present, the transient androgen serum blood level achieved may be lower or higher than that typically obtained by other routes of administration. However, the beneficial effects achieved by intranasal administration are similar to those obtained from a steady serum testosterone level of between about 20 ng/dL to about 80 ng/dL, more preferably between about 40 ng/dL to about 60 ng/dL.

A comparison of the total area under concentration-time curves (AUC) or average concentrations of serum estradiol (or testosterone) in subjects treated with intranasal estradiol (or testosterone) and subjects treated with estradiol (or testosterone) by another route, such as transdermal, provides a basis for determining the biological equivalency of different routes of administration. Where the AUCs or average concentrations are similar, despite different routes of administration or different concentration-time profiles, the biological effect achieved is often similar. Thus, in one embodiment, the invention contemplates achieving by intranasal administration of the disclosed composition an average serum estradiol concentration over 24 hours of between about 25 pg/mL and about 50 pg/mL. In nasal preparations containing the optional androgenic compound testosterone, the invention contemplates achieving an average serum testosterone concentration over 24 hours of between about 15 ng/dL and about 40 ng/dL.

The incidence of development of simple endometrial hyperplasia resulting from co-administration of a GnRH compound and unopposed estradiol was evaluated in a study described in Example 5. One-hundred twelve premenopausal women participated in a year long study where deslorelin was administered daily as a nasal spray and estradiol was administered in the form of a transdermal patch. At the end of the year endometrial biopsies were evaluated for hyperplasia. The results, which are shown in Table 5 (see Example 5 below), show that the incidence of simple hyperplasia for untreated subjects (Arm 1, placebo/placebo) was 2.2%. The incidence of simple hyperplasia for subjects treated with intranasal deslorelin and transdermal estradiol (Arms 3, 4 and 5) was 0% (Arms 3 and 5) or 4.2% (Arm 4). The incidence in combined Arms 4 and 5 was 2.0%. These data show that delivery of a GnRH compound with unopposed estrogen (that is, estrogen in the absence of a progestin) resulted in little risk of endometrial hyperplasia, with the risk no greater than that of the women in the untreated population (Arm 1). The patients in Arm 2 of the study, where estradiol was absent for the first 6 months of the study and then added for the final 6 months, had a 16.7% incidence of simple hyperplasia.

In a similar study, described in Example 6, twenty women were treated with deslorelin and unopposed estradiol. The women were divided into treatment groups to receive intranasal deslorelin and intranasal estradiol (Arm 1), intranasal deslorelin and transdermal estradiol (Arm 2), or intranasal deslorelin and intranasal estradiol plus testosterone (Arm 3). At the end of the 6 month treatment period, the endometrial response was evaluated by biopsy.

The results of the biopsies are shown in Table 6, presented below in Example 6. The endometrial tissue was proliferative in the 16 evaluable biopsies, and there was no evidence of simple endometrial hyperplasia in any of these evaluable subjects after 6 months of treatment.

The studies described in Examples 5 and 6 show that women administered a GnRH compound and an estrogen, and optionally an androgen, by non-gastrointestinal routes, and preferably intranasally or transdermally, are not at increased risk of endometrial simple hyperplasia. The data show that a GnRH compound and an estrogenic compound can be administered to premenopausal women with no increased risk of developing simple endometrial hyperplasia relative to women receiving placebo. This observation is unexpected since typically 30% of postmenopausal women treated with unopposed estrogen (0.625 mg dose) develop simple hyperplasia (Gefland, M. et al. *Obstetrics & Gynecology*, 74:398 (1989); *JAMA*, 275(5):370 (1996); Clisham, P. et al., *Obstetrics & Gynecology*, 79:196 (1992)). Premenopausal women treated with a GnRH compound and an estrogen were expected to be similar to postmenopausal women, since the GnRH compound reduces serum estradiol and serum progesterone levels. However, the data clearly demonstrated that premenopausal women treated with a GnRH compound and an estrogenic compound for an extended time period (e.g., up to one year) had no increased incidence of simple hyperplasia. Thus, addition of a progestin to the treatment regimen of a GnRH compound and an estrogenic compound in premenopausal women was not and is not needed to protect against simple endometrial hyperplasia. This observation is particularly seen in women who have no prior estrogen deprivation (compare Arms 3, 4, 5 with Arm 2 in the study describe in Example 5). The studies further suggest that such treatment can continue for a period of about 6 to 12 months or longer with no significant risk of developing simple-hyperplasia.

Based on these studies, the phrase "no significant risk" as used herein intends that fewer than about 10%, and more preferably less than 5%, still more preferably less than about 2% of premenopausal women treated with a GnRH compound and an estrogenic compound are at risk of developing simple endometrial hyperplasia. In summary, the studies show that treatment of benign gynecological disorders with a GnRH compound and an estrogenic compound and, optionally, an androgenic compound, or contraception with the two or three compounds, need not be accompanied by treatment with a progestin on a regular or periodic basis in order to protect against simple endometrial hyperplasia or cancer.

From the foregoing, it can be seen how various objects and features of the invention are met. Treatment of benign gynecological disorders and contraception by delivery of a GnRH compound, an estrogenic compound, and optionally an androgenic compound, to premenopausal women not receiving an exogenously supplied progestin on a regular or periodic basis did not increase the risk of simple endometrial hyperplasia relative to women receiving placebo.

III. EXAMPLES

The following examples further illustrate the invention described herein and are in no way intended to limit the scope of the invention.

Example 1

Preparation of Intranasal Formulation

2-Hydroxypropyl-β-cyclodextrin was added to water at a concentration of 240 mg/mL and stirred until dissolved. 17β-Estradiol was then added to the water-cyclodextrin solution at a concentration of 1.0 mg/mL. The mixture was stirred until dissolution. Testosterone at a concentration of 5.0 mg/mL was then added, and after stirring to dissolution benzalkonium chloride (0.1 mg/mL), ethylene diamine tetra acetic acid (EDTA;1 mg/mL), and sorbitol (61.6 mg/mL) were added. The mixture was stirred. Then, the GnRH compound deslorelin acetate was added at a concentration of 20 mg/mL with stirring. The volume was brought to the final desired volume and the pH was adjusted as needed. Table 2 summarizes the preparation components, concentrations, and dosages per 50 μL.

TABLE 2

Components in Exemplary Nasal Preparation

| Component | Concentration (mg/mL) | Dose per 50 μL |
|---|---|---|
| deslorelin acetate | 20 | 1.0 mg |
| estradiol | 1.0 | 50 μg |
| testosterone | 5.0 | 250 μg |
| hydroxypropyl β cyclodextrin | 240 | 12 μg |
| benzalkonium chloride | 0.1 | 5 μg |
| EDTA | 1.0 | 50 μg |
| sorbitol | 61.6 | 3.1 mg |
| water, USP | as required | |

Example 2

Intranasal Administration of Deslorelin to Premenopausal Women with Uterine Leiomyomata A 12 week study was performed to establish an effective dose of deslorelin for controlling heavy bleeding secondary to uterine leiomyomata. Forty-one women completed the study and are identified as Subject Nos. 1–41. The women were divided into test groups for treatment with intranasal deslorelin as follows:

| Group 1 | Subject Nos. 1–6 | placebo, 0 mg deslorelin |
|---|---|---|
| Group 2 | Subject Nos. 7–21 | 0.5 mg deslorelin, once per day |
| Group 3 | Subject Nos. 22–34 | 1.0 mg deslorelin, once per day |
| Group 4 | Subject Nos. 35–41 | 2.0 mg deslorelin, once per day |

An intranasal preparation consisting of deslorelin at the indicated concentration along with sorbitol (61.6 mg/mL), benzalkonium chloride (0.1 mg/mL), and water was prepared according to the procedure of Example 1. The preparation was administered with a commercially available nasal sprayer that delivered a 50 μL spray volume. The preparation was administered by application of 50 μL to each nostril once per day, for a total daily spray volume of 100 μL to give the indicated dose of deslorelin.

The average age of the premenopausal patients was 42.3, with similar distribution among groups. For one complete menstrual cycle prior to treatment, each woman completed a daily bleeding calendar. Eligible subjects were then treated with deslorelin at the assigned dosage once per day by intranasal application. During the 12 weeks of daily intranasal administration, each woman kept a daily bleeding calendar, completed quality of life questionnaires, and underwent clinical assessment and laboratory testing. The subjects were tracked for 6 weeks post-treatment for further assessment and to document time to recovery of menses after last drug treatment day. Clinical assessments included grading of nasal irritation (Table 3A), determination of uterine size (Table 3B), and serum hormone levels (Table 3C). The bleeding scores are presented in Table 3D.

TABLE 3A

Nasal Irritation

| | | Number of Study Subjects | | | |
|---|---|---|---|---|---|
| Deslorelin (mg/day) | | 0 mg | 0.5 mg | 1 mg | 2 mg |
| Baseline | None | 11 | 11 | 13 | 9 |
| | Slight | 2 | 3 | 0 | 2 |
| | Moderate | 0 | 0 | 1 | 3 |
| | Quite a bit | 0 | 0 | 0 | 0 |
| | Extreme | 0 | 0 | 0 | 0 |
| | Total | 13 | 14 | 14 | 14 |

TABLE 3A-continued

Nasal Irritation

| | | Number of Study Subjects | | | |
|---|---|---|---|---|---|
| Deslorelin (mg/day) | | 0 mg | 0.5 mg | 1 mg | 2 mg |
| End of Week 4 | None | 13 | 11 | 13 | 12 |
| | Slight | 0 | 2 | 0 | 1 |
| | Moderate | 0 | 1 | 1 | 0 |
| | Quite a bit | 0 | 0 | 0 | 1 |
| | Extreme | 0 | 0 | 0 | 0 |
| | Total | 13 | 14 | 14 | 14 |
| End of Week 8 | None | 13 | 11 | 13 | 11 |
| | Slight | 0 | 1 | 1 | 3 |
| | Moderate | 0 | 1 | 0 | 0 |
| | Quite a bit | 0 | 1 | 0 | 0 |
| | Extreme | 0 | 0 | 0 | 0 |
| | Total | 13 | 14 | 14 | 14 |
| End of Week 12 | None | 13 | 11 | 13 | 8 |
| | Slight | 0 | 2 | 0 | 5 |
| | Moderate | 0 | 0 | 0 | 1 |
| | Quite a bit | 0 | 1 | 1 | 0 |
| | Extreme | 0 | 0 | 0 | 0 |
| | Total | 13 | 14 | 14 | 14 |

TABLE 3B

Uterine Size

| Deslorelin (mg/day) | Mean Difference* |
|---|---|
| 0 mg | +11.6 |
| 0.5 mg | −109.6 |
| 1 mg | −63.6 |
| 2 mg | −246.5 |

*end of week 12 minus baseline uterine volume ($cm^3$)

TABLE 3C

Hormone Levels

| | | Estradiol (pg/mL) | Progesterone (ng/dL) | Testoserone (ng/dL) |
|---|---|---|---|---|
| Baseline | | | | |
| | 0 mg | 164 | 560 | 32 |
| | 0.5 mg | 173 | 641 | 24 |
| | 1 mg | 123 | 480 | 26 |
| | 2 mg | 184 | 337 | 34 |
| End of Week 4 | | | | |
| | 0 mg | 141 | 121 | 27 |
| | 0.5 mg | 47 | 40 | 19 |
| | 1 mg | 51 | 12 | 22 |
| | 2 mg | 14 | 12 | 16 |

TABLE 3C-continued

| | | Hormone Levels | | |
|---|---|---|---|---|
| | | Estradiol (pg/mL) | Progesterone (ng/dL) | Testoserone (ng/dL) |
| End of Week 8 | | | | |
| | 0 mg | 134 | 142 | 31 |
| | 0.5 mg | 79 | 30 | 22 |
| | 1 mg | 95 | 25 | 20 |
| | 2 mg | 31 | 14 | 20 |
| End of Week 12 | | | | |
| | 0 mg | 152 | 382 | 29 |
| | 0.5 mg | 66 | 37 | 23 |
| | 1 mg | 30 | 10 | 16 |
| | 2 mg | 30 | 13 | 20 |

TABLE 3D

| | Bleeding Score* | | | |
|---|---|---|---|---|
| | Deslorelin (mg/day) | | | |
| | 0 mg | 0.5 mg | 1 mg | 2 mg |
| Baseline Score* | 10.2 | 10.9 | 10.8 | 14.1 |
| Weeks 1–4 | 9.5 | 6.6 | 7.8 | 6.6 |
| Weeks 5–8 | 8.4 | 3.5 | 0.4 | 1.2 |
| Weeks 9–12 | 5.2** | 2.6 | 1.7 | 0.6 |

*Bleeding scores are calculated from the sum of daily diary entries for the 28 day interval prior to the reporting period. No bleeding throughout the interval is a score of 0, 'normal' menstrual flow is a score of 5, and menorrhagia is a score of 10 or greater
**25% of subjects in the placebo group dropped out of the study and a large placebo effect was observed in some of the subjects remaining on study.

Example 3

Intranasal Administration of a GnRH compound, an Estrogen, and an Androgen to Oophorectomized Women Six volunteer women with prior oophorectomies and not presently on hormone replacement therapy were recruited. Each woman was treated with 50 μL of a nasal spray preparation, prepared as described in Example 1, on two occasions separated by one week. The 50 μL dose delivered 1 mg deslorelin, 50 μg 17β-estradiol, and 250 μg testosterone. Blood samples were collected 20 minutes and 10 minutes prior to dosing on day 1 and on day 8, and then at the following intervals after dosing on each day: 10, 20, 30, 40, 60, 90, 120, 180, 240, 360, 1440 minutes. Serum estradiol and testosterone levels were determined from the samples, and the baseline corrected cumulative area under the curve from 0 to 360 minutes for each patient for each dose are presented in FIGS. 1A and 1B.

Example 4

Intranasal Administration of Deslorelin, Estradiol, and Testosterone to Premenopausal Women Nine premenopausal women, ages 20 to 45 years, were recruited and randomly divided into three test groups for a 29 day study. The patients in Group 1, Group 2, and Group 3 were treated with the intranasal preparation similar to that described in Example 1 but with deslorelin acetate concentrations of 5 mg/mL (Group 1), 10 mg/mL (Group 2), or 20 mg/mL (Group 3). The single intranasal administration consisted of a 100 μL dose delivered using a metered nasal spray device as two 50 μL sprays, one in each nostril.

An indwelling intravenous catheter was inserted in an arm vein for withdrawal of blood samples prior to drug administration and at defined intervals post administration (study day 1) of 40, 120, 240, and 480 minutes. Thereafter, weekly blood samples (study days 8, 15, and 22) were collected for determination of serum estradiol, progesterone, testosterone, and deslorelin levels. On study day 29 post administration, blood samples were drawn according to the same regimen on study day 1. After collection, all blood samples were allowed to clot at room temperature, then refrigerated. Within 24 hours of collection, serum was separated and stored frozen at −5° C. until assayed.

Serum levels of estradiol, testosterone, and progesterone were quantitated by sensitive and specific radioimmunoassay methods (Stanczyk, F. Z. et al., *Am. J Obstet. Gynecol.*, 159(6):1540 (1988); Scott et al., *Am. J Obstet. Gynecol.*, 130(7):817 (1978)). Prior to assay of the steroid hormones, serum was extracted with ethyl acetate:hexane (1:1) and for the testosterone assay further purified via Celite™ column chromatography, with 40% toluene to elute the testosterone. Procedural losses were followed by addition of 1000 dpm of the appropriate tritiated internal standard. The sensitivities of the estradiol, testosterone, and progesterone assays were 8 pg/mL, 4 ng/dL, and 10 ng/dL, respectively. Assay accuracy was demonstrated by observed parallelism between standard curves and serially diluted serum with respect to each hormone. Intra- and inter-assay coefficients of variation were 5% to 10% and 10% to 15%, respectively. Specificity of the assays was enhanced by eliminating interfering metabolites with extraction and/or chromatography and through the use of highly specific antisera.

The results of all hormone analyses are presented for each subject in Tables 4A to 4C.

TABLE 4A

| Hormone Levels for Patients Treated with 0.5 mg/mL Deslorelin | | | | | |
|---|---|---|---|---|---|
| Study Subject* | Study Day | Time (min) | Estradiol pg/mL | Testosterone ng/dL | Progesterone ng/dL |
| #1 | 1 | 0 | 61 | 31 | 110 |
| | | 40 | 91 | 142 | |
| | | 120 | | | |
| | | 240 | | | |
| | | 480 | | | |
| | 8 | | 159 | 29 | 90 |
| | 15 | | 300 | 28 | 100 |
| | 22 | | 10 | 15 | 40 |
| | 29 | 0 | 14 | 13 | 100 |
| | | 40 | 57 | 137 | |
| | | 120 | | | |
| | | 240 | | | |
| | | 480 | | | |
| | 42 | | | | 1260 |
| #2 | 1 | 0 | 33 | 18 | 100 |
| | | 40 | 42 | 43 | |
| | | 120 | | | |

TABLE 4A-continued

Hormone Levels for Patients Treated with 0.5 mg/mL Deslorelin

| Study Subject* | Study Day | Time (min) | Estradiol pg/mL | Testosterone ng/dL | Progesterone ng/dL |
|---|---|---|---|---|---|
| | | 240 | | | |
| | | 480 | | | |
| | 8 | | 130 | 25 | 50 |
| | 15 | | 160 | 25 | 40 |
| | 22 | | 39 | 19 | 50 |
| | 29 | 0 | 52 | 18 | 60 |
| | | 40 | 50 | 20 | |
| | | 120 | | | |
| | | 240 | | | |
| | | 480 | | | |
| | 42 | | | | 40 |
| #3 | 1 | 0 | 54 | 21 | 90 |
| | | 40 | 128 | 190 | |
| | | 120 | | | |
| | | 240 | | | |
| | | 480 | | | |
| | 8 | | 85 | 39 | 110 |
| | 15 | | 98 | 36 | |
| | 22 | | 37 | 22 | 40 |
| | 29 | 0 | 103 | 86 | 70 |
| | | 40 | 112 | 142 | |
| | | 120 | | | |
| | | 240 | | | |
| | | 480 | | | |
| | 42 | | | | |

*Treated with the nasal preparation of Example 2 having 0.5 mg/mL deslorelin acetate.

TABLE 4B

Hormone Levels for Patients Treated with 1.0 mg/mL Deslorelin

| Study Subject* | Study Day | Time (min) | Estradiol pg/mL | Testosterone ng/dL | Progesterone ng/dL |
|---|---|---|---|---|---|
| #4 | 1 | 0 | 73 | 21 | 40 |
| | | 40 | 98 | 81 | |
| | | 120 | | | |
| | | 240 | | | |
| | | 480 | | | |
| | 8 | | 167 | 31 | 50 |
| | 15 | | 91 | 33 | 50 |
| | 22 | | 86 | 24 | 50 |
| | 29 | 0 | 40 | 23 | 60 |
| | | 40 | 126 | 144 | |
| | | 120 | | | |
| | | 240 | | | |
| | | 480 | | | |
| | 42 | | | | |
| #5 | 1 | 0 | 73 | 21 | 220 |
| | | 40 | 227 | 250 | |
| | | 120 | | | |
| | | 240 | | | |
| | | 480 | | | |
| | 8 | | 26 | 19 | 50 |
| | 15 | | 27 | 23 | 30 |
| | 22 | | 132 | 37 | 50 |
| | 29 | 0 | 45 | 25 | 40 |
| | | 40 | 98 | 102 | |
| | | 120 | | | |
| | | 240 | | | |
| | | 480 | | | |
| | 42 | | | | |
| #6 | 1 | 0 | 51 | 20 | 60 |
| | | 40 | 181 | 174 | |
| | | 120 | | | |
| | | 240 | | | |
| | | 480 | | | |
| | 8 | | 45 | 36 | 80 |
| | 15 | | 18 | 20 | 70 |
| | 22 | | 48 | 16 | 60 |

TABLE 4B-continued

Hormone Levels for Patients Treated with 1.0 mg/mL Deslorelin

| Study Subject* | Study Day | Time (min) | Estradiol pg/mL | Testosterone ng/dL | Progesterone ng/dL |
|---|---|---|---|---|---|
| | 29 | 0 | 29 | 20 | 100 |
| | | 40 | 89 | 98 | |
| | | 120 | | | |
| | | 240 | | | |
| | | 480 | | | |
| | 42 | | | | |

*Treated with the nasal preparation of Example 2 having 1.0 mg/mL deslorelin acetate.

TABLE 4C

Hormone Levels for Patients Treated with 2.0 mg/mL Deslorelin

| Study Subject* | Study Day | Time (min) | Estradiol pg/mL | Testosterone ng/dL | Progesterone ng/dL |
|---|---|---|---|---|---|
| #7 | 1 | 0 | 32 | 14 | 90 |
| | | 40 | 141 | 149 | |
| | | 120 | | | |
| | | 240 | | | |
| | | 480 | | | |
| | 8 | | 21 | 13 | 50 |
| | 15 | | 16 | 14 | 60 |
| | 22 | | 12 | 9 | 40 |
| | 29 | 0 | 23 | 10 | 70 |
| | | 40 | 40 | 24 | |
| | | 120 | | | |
| | | 240 | | | |
| | | 480 | | | |
| | 42 | | | | |
| #8 | 1 | 0 | 61 | 15 | 80 |
| | | 40 | 191 | 244 | |
| | | 120 | | | |
| | | 240 | | | |
| | | 480 | | | |
| | 8 | | 149 | 30 | 50 |
| | 15 | | 302 | 39 | 70 |
| | 22 | | 22 | 22 | 150 |
| | 29 | 0 | 90 | 25 | 70 |
| | | 40 | 117 | 88 | |
| | | 120 | | | |
| | | 240 | | | |
| | | 480 | | | |
| | 42 | | | | |
| #9 | 1 | 0 | 37 | 21 | 30 |
| | | 40 | 152 | 241 | |
| | | 120 | | | |
| | | 240 | | | |
| | | 480 | | | |
| | 8 | | 158 | 110 | 20 |
| | 15 | | 18 | 18 | 20 |
| | 22 | | 24 | 15 | 10 |
| | 29 | 0 | 29 | 14 | 20 |
| | | 40 | 143 | 132 | |
| | | 120 | | | |
| | | 240 | | | |
| | | 480 | | | |
| | 42 | | | | |

*Treated with the nasal preparation of Example 2 having 2.0 mg/mL deslorelin acetate.

Example 5
Intranasal Delivery of GnRH Compound with Transdermal Co-administration of Estradiol Example 5 describes an intranasally delivered GnRH compound with co-administration of 17β-estradiol. Premenopausal females (n=265) were recruited for participation in a 12 month double blind study. The women were randomly assigned to treatment in one of the following five study arms:

| Arm 1 | placebo/placebo |
| --- | --- |
| Arm 2 | deslorelin, intranasal/placebo for 6 months; then crossed over to arm 5 |
| Arm 3 | deslorelin, intranasal/25 μg estradiol transdermal |
| Arm 4 | deslorelin, intranasal/50 μg estradiol transdermal |
| Arm 5 | deslorelin, intranasal/75 μg estradiol transdermal |

Deslorelin at a daily dose of 1 mg was administered intranasally using a conventional metered delivery device. Estradiol was administered transdermally using a commercially-available twice-weekly patch that delivered either 25 μg estradiol or 50 μg estradiol per day. Subjects in Arm 5 wore two patches, one at each dosage, to achieve the 75 μg dose.

At the end of the 12 month treatment period an endometrial biopsy was taken for analysis of the endometrial morphology. The results are shown in Table 5.

TABLE 5

Incidence of Simple Hyperplasia from Endometrial Biopsy

| | Arm | | | | | |
| --- | --- | --- | --- | --- | --- | --- |
| | 1 | 2 | 3 | 4 | 5 | 4&5 |
| No. of subjects with simple hyperplasia | 1 | 2 | 0 | 1 | 0 | 1 |
| Total no. of subjects studied | 45 | 12 | 6 | 24 | 25 | 49 |
| Proportion of subjects with simple hyperplasia | 0.022 | 0.167 | 0.000 | 0.042 | 0.000 | 0.020 |

Example 6

Intranasal Delivery of GnRH Compound with Transdermal or Intranasal Co-administration of Estradiol Twenty premenopausal women were recruited and randomly assigned for treatment as follows:

| Arm 1 | deslorelin, intranasal and estradiol transdermal | n = 5 |
| --- | --- | --- |
| Arm 2 | deslorelin and estradiol, intranasal | n = 7 |
| Arm 3 | deslorelin, estradiol, and testosterone intranasal | n = 8 |

The Arm 1 intranasal formulation contained 1 mg deslorelin; the Arm 1 estradiol was delivered transdermally from a twice-weekly commercially-available 50 μg/day estradiol patch. The intranasal formulation used in Arms 2 and 3 contained 1 mg deslorelin and 300 μg estradiol (Arm 2), and additionally 275 μg testosterone (Arm 3), formulated in a similar manner as that described in Example 1.

After the six month treatment period the incidence of endometrial hyperplasia was evaluated by biopsy in 20 subjects. The results are shown in Table 6.

TABLE 6

Endometrial Response

| | Hyperplasia | Proliferative | Atrophic | Insufficient Tissue | Refused |
| --- | --- | --- | --- | --- | --- |
| Baseline | 0 | 17 | 0 | 3 | 0 |
| Month 6 | 0 | 16 | 0 | 3 | 1 |

Although the invention has been described with respect to particular embodiments, it will be apparent to those skilled in the art that various changes and modifications can be made without departing from the invention.

What is claimed is:

1. A method of treating a benign gynecological disorder in a patient population composed of premenopausal women, comprising, administering a gonadotropin releasing hormone (GnRH) compound, in an amount effective to suppress ovarian estrogen and progesterone production, and an estrogenic compound, in an amount effective to prevent signs and symptoms of estrogen deficiency, along with, optionally, an androgen, in an amount effective to prevent signs and symotoms of androgen deficiency, for a time oeriod of more than about 4 months, with the proviso that women in the patient population do not receive an exogenously supplied progestin during said time period to prevent endometrial hyperplasia.

2. The method of claim 1, wherein the GnRH compound is a GnRH peptide agonist, and the compound is administered intranasally.

3. The method of claim 1, wherein the GnRH compound is selected from the group consisting of deslorelin, leuprolide, nafarelin, goserelin, decapeptyl, buserelin, histrelin, gonadorelin, abarelix, cetrorelix, azaline B, and degarelix, and analogs thereof.

4. The method of claim 3, wherein the GnRH compound is administered by an intranasal route, and the estrogenic compound is 17β-estradiol administered by a transdermal route, at a daily dose between 0.025 and 0.1 mg.

5. The method of claim 4, which further includes co-administering testosterone transdermally, at a daily dose sufficient to increase serum testosterone to the premenopausal range of between 15 and 80 ng/dL.

6. The method of claim 3, wherein the GnRH compound and the estrogenic compound are co-administered intranasally, in an aerosol spray containing a daily spray volume between 30 and 200 μL, and between 0.15 and 0.6 mg of 17β-estradiol.

7. The method of claim 6, which further includes co-administering testosterone intranasally in the aerosol spray at a daily dosage of between 0.15 and 1 mg testosterone.

* * * * *